(12) United States Patent
Covington et al.

(10) Patent No.: US 10,454,347 B2
(45) Date of Patent: Oct. 22, 2019

(54) COMPACT HEIGHT TORQUE SENSING ARTICULATION AXIS ASSEMBLY

(71) Applicant: Auris Health, Inc., Redwood City, CA (US)

(72) Inventors: Travis Covington, Sunnyvale, CA (US); Colin Wilson, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 356 days.

(21) Appl. No.: 15/582,390

(22) Filed: Apr. 28, 2017

(65) Prior Publication Data

US 2017/0312481 A1    Nov. 2, 2017

Related U.S. Application Data

(60) Provisional application No. 62/329,617, filed on Apr. 29, 2016.

(51) Int. Cl.
   *A61M 25/01*    (2006.01)
   *H02K 11/24*    (2016.01)
   (Continued)

(52) U.S. Cl.
   CPC .............. *H02K 11/24* (2016.01); *A61B 34/30* (2016.02); *A61B 90/06* (2016.02); *F16H 57/08* (2013.01); *F16H 57/082* (2013.01); *H02K 7/116* (2013.01); *H02K 11/21* (2016.01); *A61B 2017/00323* (2013.01); *A61B 2034/301* (2016.02);
   (Continued)

(58) Field of Classification Search
   CPC .... A61B 2017/00323; A61B 2034/301; A61B 2090/064; A61B 2090/066; A61B 34/30; A61B 90/06; F16H 2057/016; F16H 2057/02034; F16H 2057/02039; F16H 57/08; F16H 57/082; H02K 11/21; H02K 11/24; H02K 7/116
   See application file for complete search history.

(56) References Cited

U.S. PATENT DOCUMENTS 2,556,601 A    6/1951    Schofield
2,566,183 A    8/1951    Forss
(Continued)

FOREIGN PATENT DOCUMENTS

CN    101500470    8/2009
CN    102665590    9/2012
(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

*Primary Examiner* — Muhammad S Islam
(74) *Attorney, Agent, or Firm* — Knobbe, Martens, Olson & Bear LLP

(57) ABSTRACT

A compact height torque sensing articulation axis assembly is disclosed herein having a torque sensor, an assembly mounting flange, a motor, a motor gearbox, a gearbox output shaft, an encoder, and a cable. The assembly may sense tension on robotic catheter pullwires in an articulating catheter and/or torque on a robotic output axis using the torque sensor. Disclosed embodiments may advantageously be used to achieve small, lightweight robotic catheter systems.

34 Claims, 16 Drawing Sheets

(51) Int. Cl.
  *A61B 90/00*   (2016.01)
  *H02K 7/116*   (2006.01)
  *H02K 11/21*   (2016.01)
  *A61B 34/30*   (2016.01)
  *F16H 57/08*   (2006.01)
  *A61B 17/00*   (2006.01)
  *F16H 57/02*   (2012.01)
  *F16H 57/01*   (2012.01)

(52) U.S. Cl.
  CPC ... *A61B 2090/064* (2016.02); *A61B 2090/066* (2016.02); *F16H 2057/016* (2013.01); *F16H 2057/02034* (2013.01); *F16H 2057/02039* (2013.01)

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage et al. |
| 5,559,294 A | 9/1996 | Hoium et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,921,968 A | 7/1999 | Lampropoulos et al. |
| 5,967,934 A | 10/1999 | Ishida et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,291,791 B2 | 10/2012 | Light et al. |
| 8,746,252 B2 | 6/2014 | McGrogan et al. |
| 8,961,533 B2 | 2/2015 | Stahler et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0117017 A1 | 8/2002 | Bernhardt et al. |
| 2002/0161355 A1 | 10/2002 | Wollschlager |
| 2002/0177789 A1 | 11/2002 | Ferry et al. |
| 2004/0015053 A1 | 1/2004 | Bieger |
| 2004/0152972 A1 | 8/2004 | Hunter |
| 2004/0243147 A1 | 12/2004 | Lipow |
| 2005/0183532 A1 | 8/2005 | Najaf et al. |
| 2005/0222554 A1 | 10/2005 | Wallace et al. |
| 2006/0111692 A1 | 5/2006 | Hlavka et al. |
| 2006/0201688 A1 | 9/2006 | Jenner et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0112355 A1 | 5/2007 | Salahieh |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0171371 A1* | 7/2009 | Nixon ............... A61B 34/30 606/130 |
| 2009/0247944 A1 | 10/2009 | Kirschenman et al. |
| 2010/0030023 A1 | 2/2010 | Yoshie |
| 2010/0069833 A1 | 3/2010 | Wenderow et al. |

(56) References Cited

U.S. PATENT DOCUMENTS

| | | |
|---|---|---|
| 2010/0073150 A1 | 3/2010 | Olson et al. |
| 2010/0130987 A1 | 5/2010 | Wenderow et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071621 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0239012 A1 | 9/2012 | Laurent et al. |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0222019 A1 | 8/2014 | Brudnick |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364670 A1 | 12/2014 | Alvarez et al. |
| 2014/0379000 A1 | 12/2014 | Romo et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0297864 A1 | 10/2015 | Kokish et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0001038 A1 | 1/2016 | Romo et al. |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0007343 A1 | 1/2017 | Yu |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0290631 A1 | 10/2017 | Lee et al. |
| 2017/0296784 A1 | 10/2017 | Kokish |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 3 025 630 | 6/2016 |
| JP | 2009-139187 | 6/2009 |
| JP | 2010-046384 | 3/2010 |
| WO | WO 02/074178 | 9/2002 |
| WO | WO 09/092059 | 7/2009 |
| WO | WO 11/005335 | 1/2011 |
| WO | WO 13/179600 | 12/2013 |
| WO | WO 15/127231 | 8/2015 |

* cited by examiner

COMPACT HEIGHT TORQUE SENSING ARTICULATION AXIS ASSEMBLY

CROSS-REFERENCE TO RELATED APPLICATIONS

This application claims priority to U.S. Provisional Application 62/329,617, filed Apr. 29, 2016, the entirety of which is hereby incorporated by reference herein for any and all purposes as if set forth herein in its entirety. Embodiments described in this application may be used in combination or conjunction with the subject matter described in one or more of the following, each of which is hereby fully incorporated by reference for any and all purposes as if set forth herein in their entireties:

U.S. patent application Ser. No. 13/835,136, filed Mar. 15, 2013, entitled "ACTIVE DRIVE MECHANISM FOR SIMULTANEOUS ROTATION AND TRANSLATION;"

U.S. patent application Ser. No. 13/839,967, filed Mar. 15, 2013, entitled "VASCULAR REMOTE CATHETER MANIPULATOR;"

U.S. patent application Ser. No. 14/214,711, filed Mar. 14, 2013, entitled "CATHETER TENSION SENSING;" and U.S. Pat. No. 9,173,713, issued Nov. 3, 2015, entitled "TORQUE-BASED CATHETER ARTICULATION."

BACKGROUND

Robotic surgical systems and devices are well suited for use in performing minimally invasive medical procedures. For example, a robotic surgical system may be utilized to facilitate imaging, diagnosis, and treatment of tissues and vessels which may lie deep within a patient, and which may be preferably accessed only via naturally-occurring pathways such as blood vessels or the gastrointestinal tract.

One such robotic surgical system that may be utilized in a minimally invasive procedure is a robotic catheter system. A robotic catheter system utilizes a robot, external to the patient's body cavity, to insert a catheter through a small incision in a patient's body cavity and guide the catheter to a location of interest. Catheters may be steerable for movement in multiple axes, including axial translation (i.e., insertion and retraction), axial rotation, and deflection/articulation (including radial bending in multiple directions). To accomplish steering, one or more pullwires are attached to a distal articulating section of a catheter and extend through the catheter to at least the catheter's proximal end. The distal tip of the catheter may then be controlled via the pullwires (e.g., by selectively operating tensioning control elements, which control tension and/or displacement of the pullwires within the catheter instrument).

Kinematic modeling is utilized to predict catheter tip movement within the patient anatomy. The amount of displacement of a pullwire is generally proportional to the amount of articulation, enabling modeling of predicted catheter tip movement. However, at times, pullwire displacement may not result in the expected catheter tip articulation. Various elements can affect the amount of articulation for a given pullwire actuation, including the presence of unanticipated or un-modeled constraints imposed by the patient's anatomy, particularly given the tortuous path that the catheter must traverse. Additionally, pullwire displacement may result in an increase in pullwire tension rather than a change in catheter articulation if there is undetected slack in the pullwire. When unanticipated and un-modeled conditions or constraints exist, kinematic modeling may not accurately predict catheter tip movement leading to errors. Minimization of differences between actual and predicted kinematic functions is thus desirable to achieve a highly controllable robotic surgical system.

In robotic catheter systems, output shafts that actuate the pullwires connect the transmission elements in the catheter (e.g., pullwires) to motors in the robotic system. For the reasons discussed above, detecting load and/or torque on the output shafts as well as monitoring and controlling pullwire displacement may more accurately predict catheter tip movement than monitoring pullwire displacement alone.

Currently, some examples of robotic catheter systems are equipped with a rotary or shaft encoder. While the rotational position of the output shaft may be determined from the encoder, the torque applied at the output shaft may not be able to be precisely calculated because of variations in transmission efficiency and the effects of perturbations on the system due to catheter construction shape and use. Moreover, the encoder may not provide accurate information on load. For example, external forces on the catheter can change the loading on the catheter pullwires and, for a fixed position of the output shaft, in turn may change the torsion loading on the output shafts. As such, a need exists for improved load and/or torque sensing on the output shaft.

Another example of a robotic catheter system that utilizes a robot, external to the patient's body cavity, to insert and retract catheters and guidewires through a small incision in a patient's body cavity and guides the catheters/wires to a location of interest is described in U.S. application Ser. No. 13/835,136 and U.S. Ser. No. 13/839,967 (previously incorporated by reference). To accomplish linear translation (i.e., insertion and/or retraction) of the catheter or guidewire, this robotic catheter system uses a set of motors to rotate opposing wheels or rollers in opposite directions. In this system, the motors rotate to control the rate of linear translation. The angular rotation of the roller may be used to control the linear displacement of the catheter or guidewire. In other words, the linear travel of the catheter or wire is generally proportional to the angular rotation of the rollers. However, if higher insertion forces are encountered, the catheters or guidewires may slip between the rollers and not be inserted as far as intended. Some robotic systems incorporate torque sensors on the motors to measure the torque required to insert the catheter or guidewire.

In many robotic catheter systems, steering of the catheter is controlled by an instrument driver. The instrument driver may contain, for example, the one or more motors that drive the one or more output shafts. There is a need to keep the instrument driver of the robotic catheter system small so that it does not interfere with the available workspace in a surgical suite or catheterization lab. There are size constraints on all dimensions of the instrument driver. If the instrument driver of a surgical system is too wide, then it will obscure certain parts of the anatomy for an external imaging source such as a fluoroscopy system. If the instrument driver is too long, then the carriages cannot come close enough together on telescoping robotic systems, and the inner catheter cannot be inserted as far into the outer catheter, resulting in a need for longer catheters and a lack of control. If the instrument driver is too tall, then the angle of entry into the patient becomes too steep, resulting in access site injuries such as bleeding or hematomas.

A robotic vascular catheter system typically includes elongate members that include a sheath catheter, a leader catheter, and a guidewire. More generally, a robotic system for driving an elongate member into a patient lumen typically includes an outer elongate member, an inner elongate member, and a guidewire. Each is separately controllable and may telescope with respect to one another. For instance, a sheath carriage controls operation of the sheath (or outer elongate member) and is moveable along a generally axial direction aligned axially with the patient (referred to herein as the insertion axis), and a leader carriage controls operation of the leader (or inner elongate member) and a guidewire and is likewise moveable about the insertion axis of the patient. Typically, the leader carriage and the sheath carriage are positioned on an instrument driver often referred to as a remote catheter manipulator (RCM), which is supported by a setup joint (SUJ). Because the sheath carriage and leader carriage are traditionally aligned along the insertion axis, this configuration results in the RCM taking up significant space over the patient. If the RCM is too large, the system can interfere with other system operations (such as operation of the C-arm and/or monitors).

For instance, in some minimally-invasive surgery procedures, an imaging device such as a fluoroscopy system may be required in addition to the RCM. In such procedures, the imaging device may scan and image the entire body from the insertion site to the site of the medical procedure. If the RCM is too large, the RCM may obstruct the imaging device's ability to capture the entire desired imaging field.

Accordingly, despite the benefits of torque sensing, many robotic catheter systems do not have torque sensing due to the size constraints mentioned here. Therefore, there remains a need for a compact torque sensor that can provide the torque information needed to better control the catheter without increasing the size of the instrument driver.

SUMMARY

In some embodiments, a robotic surgical system may include a control system electrically connectable to an input device and configured to receive information for positioning or orienting a catheter from the input device; the system may further include an instrument driver operatively connected to the control system. The instrument driver may include one or more articulation drive assemblies. Each articulation drive assembly may include: a motor configured to provide rotary output to actuate movement of an elongate member or other component of the surgical system; a gearbox configured to modify the rotary output of the motor; and a reactive torque sensor coaxial with and radially surrounding at least a portion of the rotary output motor and/or the gearbox. The motor may be at least partially within the reactive torque sensor to minimize height of the articulation drive assembly. The control system may be configured to actuate the motor in response to the information, from the input device, to drive an output shaft in communication with the elongate member. The instrument driver may be configured to determine an output shaft torque imparted by the output shaft to the elongate member. The reactive torque sensor may be coaxial with, and at least partially radially surround, both the rotary output motor and the gearbox. At least one of the gearbox and the motor may be mounted to the reactive torque sensor by a first mounting flange. The articulation drive assembly may be mounted to the instrument driver housing by the second mounting flange of the torque sensor. The first and second flanges may be configured to ground torque loads. The reactive torque sensor may further include at least one load cell configured to measure the output shaft torque. The articulation drive assembly may be configured to adjust a pullwire tension to impart motion to a tip of a catheter or elongate device or alternatively may be configured to rotate a drive wheel or roller on an active drive device to insert, retract, or rotate an elongate device. The system may further include a motor cable wrapped at least once around and communicatively coupled to at least one of the motor, the gearbox, and the torque sensor. The cable may be clock spring wound.

In some embodiments, an instrument driver for an elongate member of a robotic surgical system may include: a gearbox configured to actuate movement of the elongate member by driving an output shaft in communication with the elongate member; a rotary output motor axially-aligned with the gearbox and configured to drive the gearbox; and a reactive torque sensor radially surrounding the gearbox and configured to determine an output shaft torque imparted by the output shaft to the elongate member. The reactive torque sensor may provide a grounded mounting structure for the motor and gearbox. The reactive torque sensor may have a length shorter than the combined length of the motor and gearbox. The reactive torque sensor may have a length shorter than the gearbox. The rotary output motor may be a brushless low-profile outrunner motor. The instrument driver may further include a clock-spring style wound flat flex cable assembly configured to provide an electrical connection to the motor.

A method of measuring an output torque may include providing a rotary output shaft configured to actuate an elongate member, providing at least one output motor configured to actuate movement of the elongate member by driving the output shaft, and determining an output torque of the output shaft using a torque sensor disposed in surrounding relation to the motor. The method may further include establishing the sensor input as a reactive torque sensor input, the reactive torque sensor input measured via a connection between the reactive torque sensor and the motor. The method may further include providing a gearbox coupled to the motor. The method may further include modifying the output torque by sending a signal to the motor. The signal may be sent to the motor over a clock-spring style wound flat flex cable.

DETAILED DESCRIPTION

Figure 1:
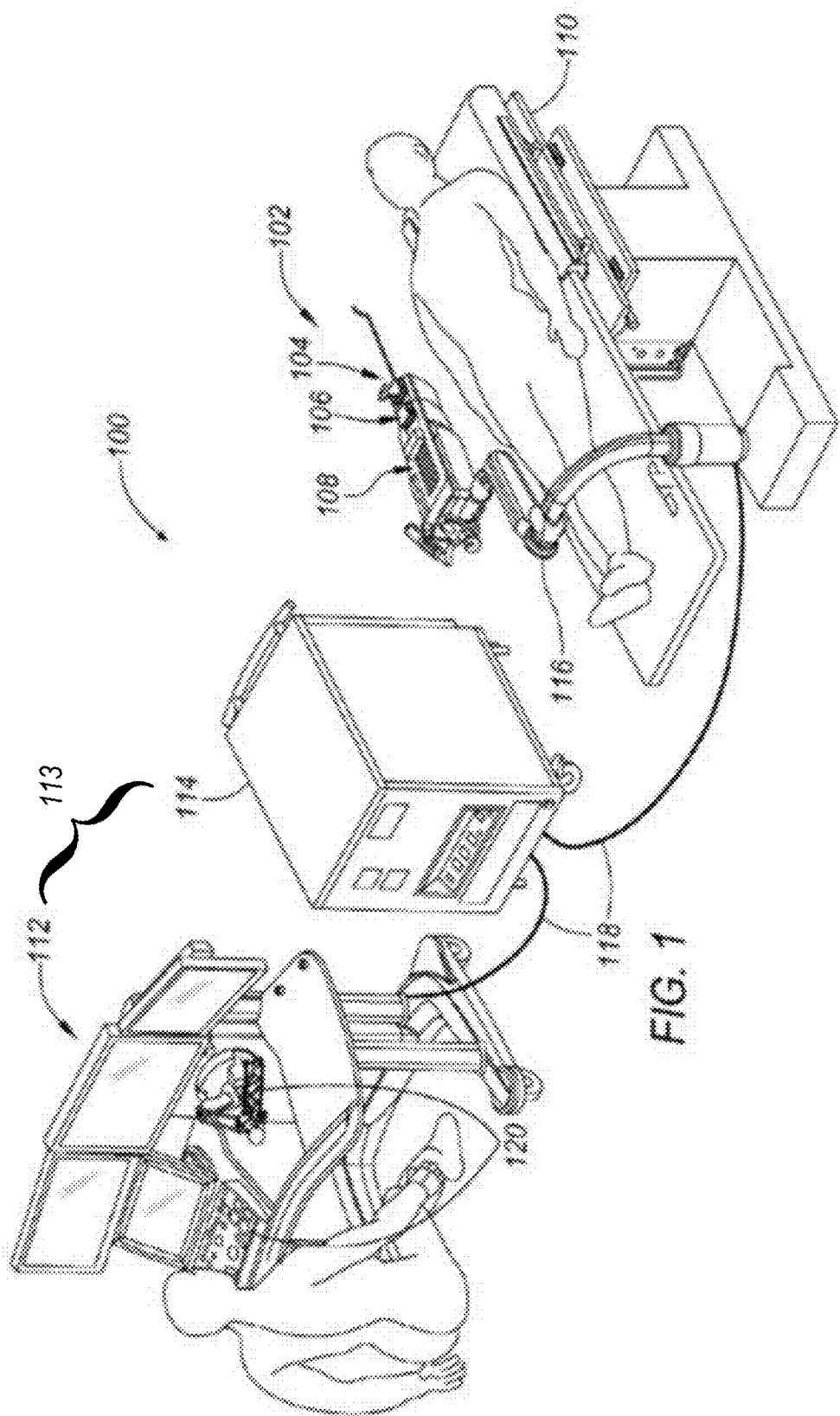
FIG. 1 is a perspective view of an exemplary robotic surgical system.

Referring now to the discussion that follows and also to the drawings, illustrative approaches to the disclosed assemblies are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

As used herein, the term "catheter" may refer to any flexible elongate medical instrument.

Referring to FIG. 1, a robotic surgical system 100 is illustrated in which an apparatus, a system, and/or method may be implemented according to various exemplary illustrations. The system 100 may include a robotic catheter assembly 102 having one or more elongate members such as a sheath instrument 104 and/or a catheter instrument 106. The catheter assembly 102 and the sheath instrument 104 are controllable using a robotic instrument driver (or drivers) 108 (generally referred to as "instrument driver"). During use, a patient is positioned on an operating table or surgical bed 110 to which the robotic instrument driver 108 is coupled or mounted. In the illustrated example, the system 100 includes an operator workstation 112, an electronics rack 114 including a control computer (not shown), a setup joint mounting brace 116, and instrument driver 108. A surgeon is seated at the operator workstation 112 and can monitor the surgical procedure, patient vitals, and control one or more catheter devices.

The operator workstation 112 may include a computer monitor to display an object, such as a catheter displayed within or relative to a body cavity or organ (e.g., a chamber of a patient's heart). In one example, an operator uses one or more input devices 120 to control the position of a catheter or other elongate instrument. In response to actuation of the input device by a user, the input device can output information for the desired position or orientation of the elongate instrument, including the three-dimensional spatial position and/or orientation of the distal end of a steerable elongate instrument. System components, including the operator workstation, electronics rack and the instrument driver, may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while located away from or remotely from radiation sources. Because of the option for wireless or networked operation, the surgeon may even be located remotely from the patient in a different room or building.

The operator workstation 112, the electronic rack 114 and/or the instrument driver can form part of a control system 113. As will be explained below, the control system 113 can be configured to actuate a motor within the instrument driver 108 in response to information from the one or more input devices 120 and/or the instrument driver to drive an output shaft that can be used to control movement of one or more elongated members such as a sheath instrument 104 and/or an catheter instrument 106. The control system 113 can reside in one or more of the operator workstation 112, the electronic rack 114 and/or the instrument driver and/or in other components.

Figure 2:
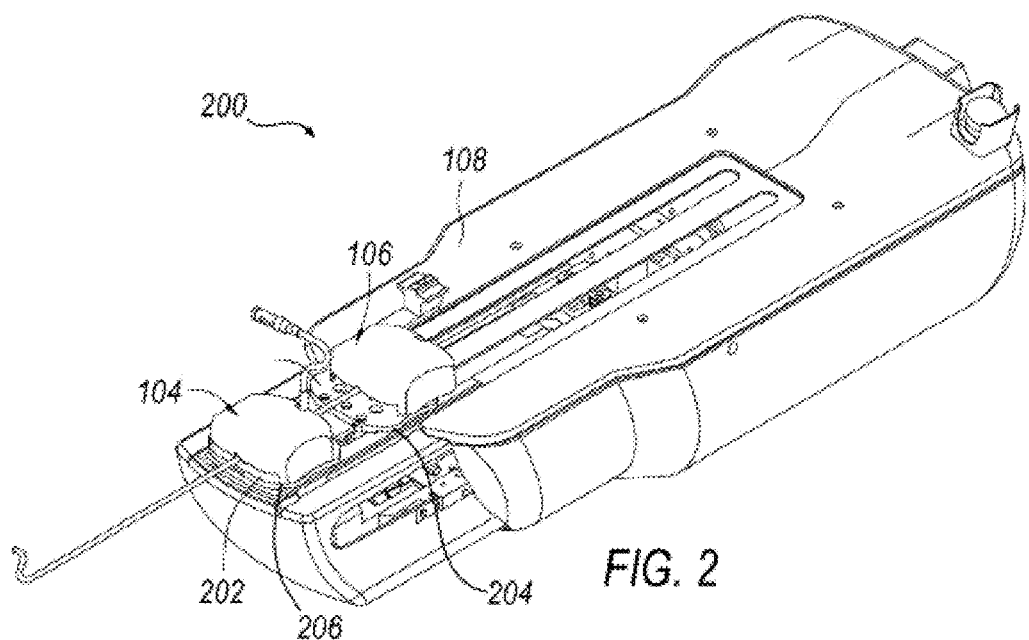
FIG. 2 is a perspective view of an exemplary catheter assembly of the surgical system of FIG. 1.

Referring now to FIG. 2, motors within instrument driver 108 are controlled such that carriages coupled to mounting plates 204, 206 are driven forwards and backwards on bearings. As a result, one or more elongate instruments can be controllably manipulated while inserted into the patient or retracted out of the patient. The instrument driver 108 contains motors that may be activated to control bending of the one or more elongate instruments as well as the orientation of the distal tips, and optionally, tools mounted at the distal tips.

Figure 3:
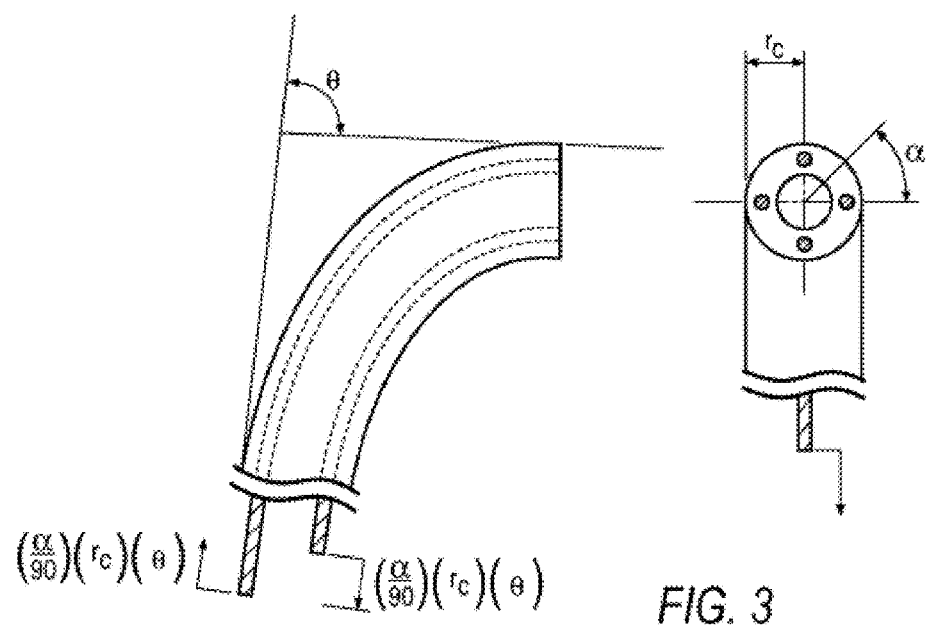
FIG. 3 is a schematic showing a kinematic relationship between pullwire displacement and catheter tip articulation.

The articulation of catheters is normally performed by actuating pullwires that extend the length of the catheter and are attached to an articulating section of a catheter at or near the catheter's distal end. In order to articulate the catheter, the pullwire is manipulated and displaced at the proximal end to articulate the distal end of the catheter. Typically, the amount that an articulating section of a catheter articulates is determined by calculating the change in path length that an actuating pullwire takes. For a straight catheter, that length is equal to the articulating section, $L_o$. As the catheter bends (where $\alpha$ is the angle from the neutral axis, $r_c$ is the radius of the catheter, and $\tau$ is the articulation angle), the path length is equal to $L_o - \cos(\alpha/90)*r_c*\tau$. The difference— $(\alpha/90)*r_c*\tau$—is the distance the pullwire must be actuated to make a catheter articulate to an angle $\tau$, as illustrated in FIG. 3. From this concept, further solid mechanic and kinematic modeling is used via algorithms in the control computer to convert a desired catheter position or orientation as provided by the user into commands to the instrument driver to rotate motors designated for each pullwire.

Figure 4:
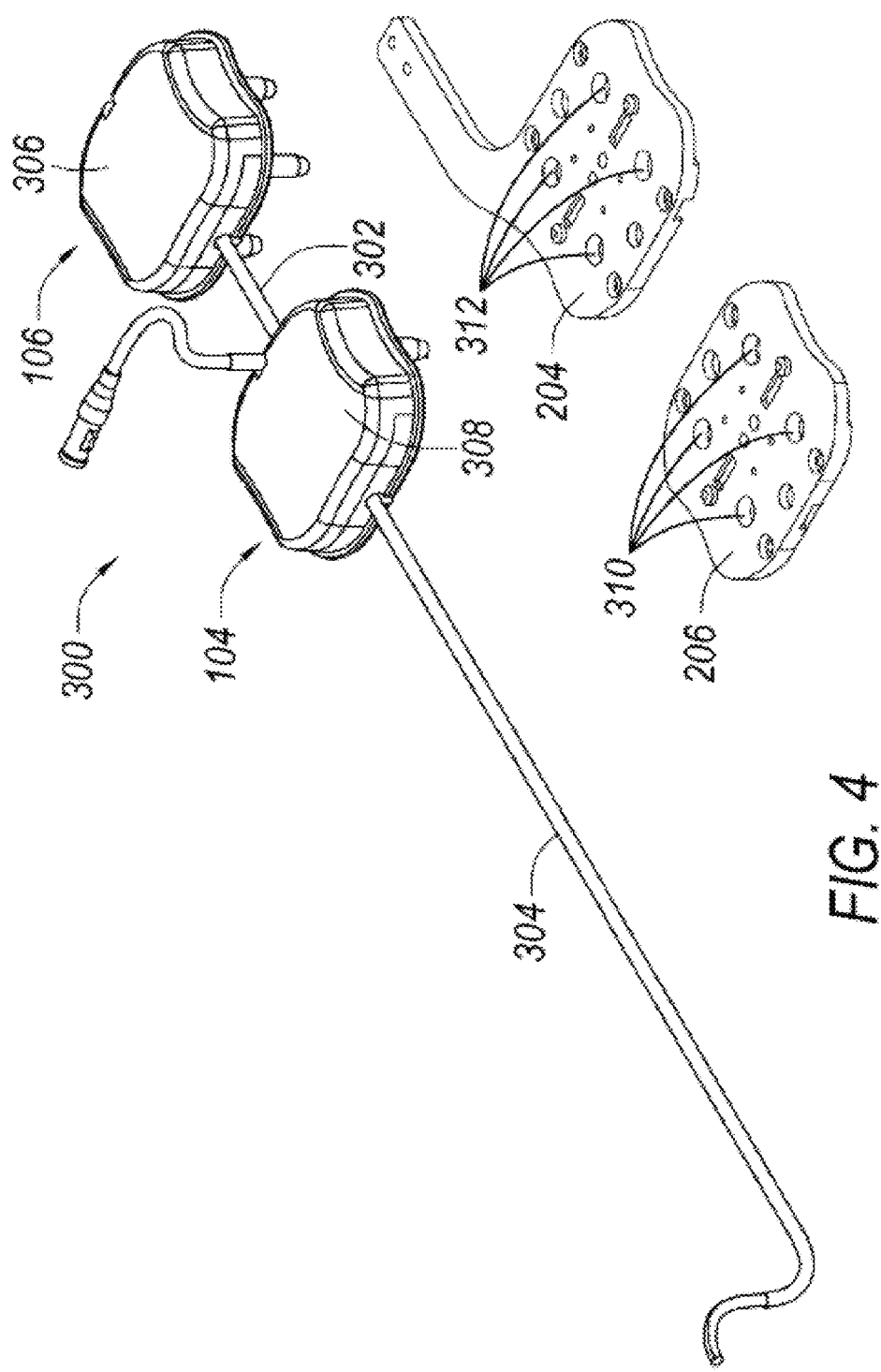
FIG. 4 is a partially-exploded view of the catheter assembly of FIG. 2.
Figure 5:
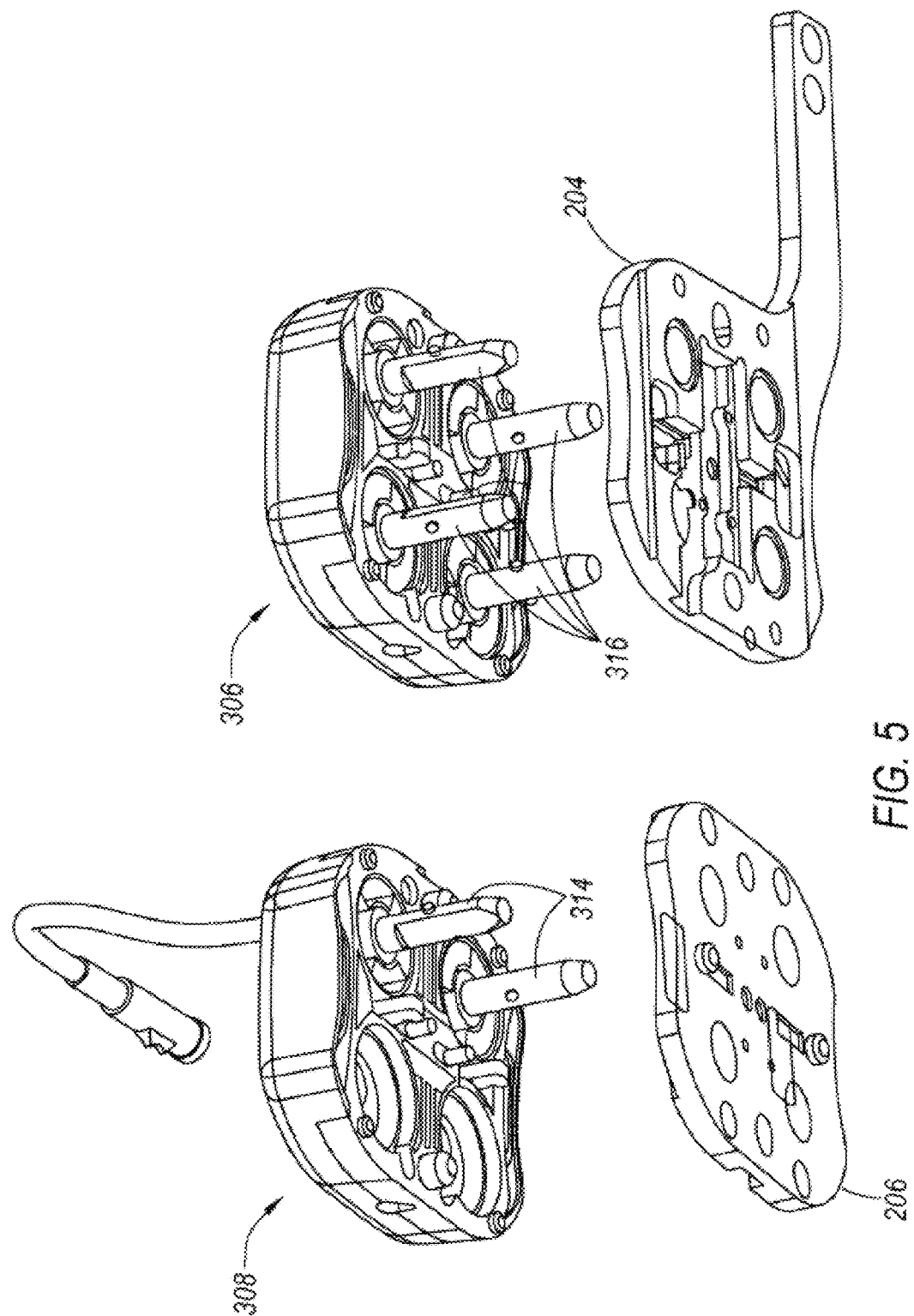
FIG. 5 is a partially-exploded view of the catheter assembly of FIG. 2.

In order to prepare a catheter to be manipulated and articulated by an instrument driver, the catheter is mounted to the instrument driver. More particularly, the catheter is provided with a splayer, which is mounted onto an interface plate. In some embodiments, as shown in FIG. 4, a sheath splayer 308 is placed onto a sheath interface plate 206 and a guide splayer 306 is placed onto a guide interface plate 204. In the illustrated example, each interface plate 204, 206 has respectively four openings 310, 312 that are designed to receive corresponding drive shafts 314, 316 (FIG. 5 illustrates an underside perspective view of shafts 314, 316) attached to and extending from pulley assemblies of the splayers 308, 306. The drive shafts 314, 316 are each coupled to a respective motor within the instrument driver 108 (see, e.g., FIG. 2).

Figure 6:
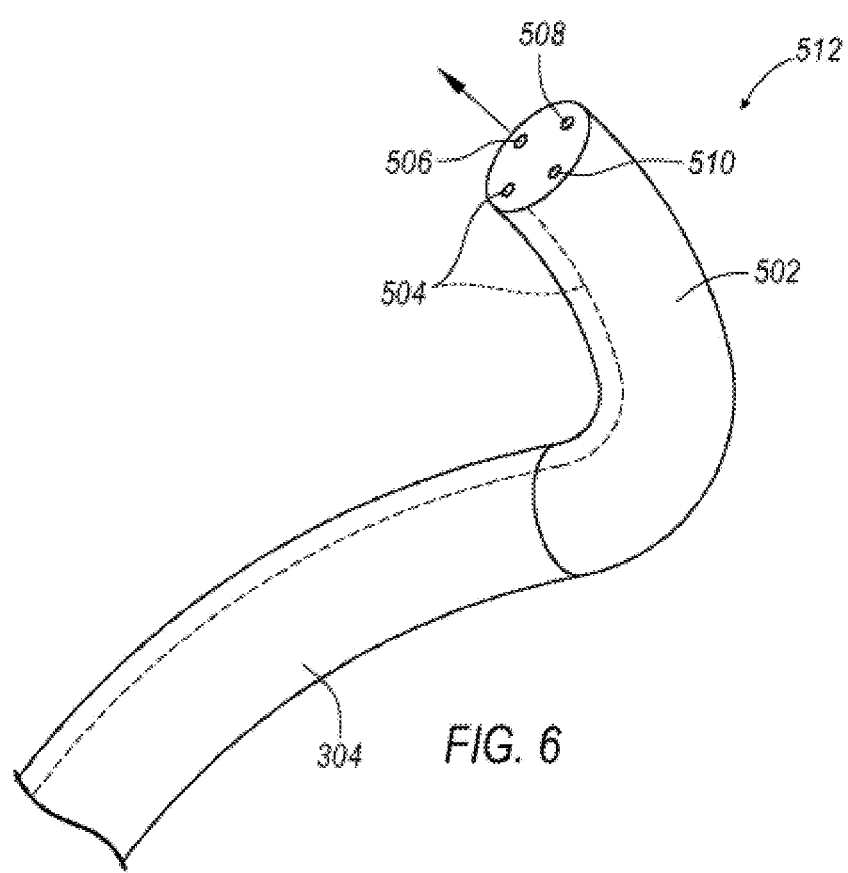
FIG. 6 is a perspective view of an exemplary steerable catheter with pullwires.
Figure 7:
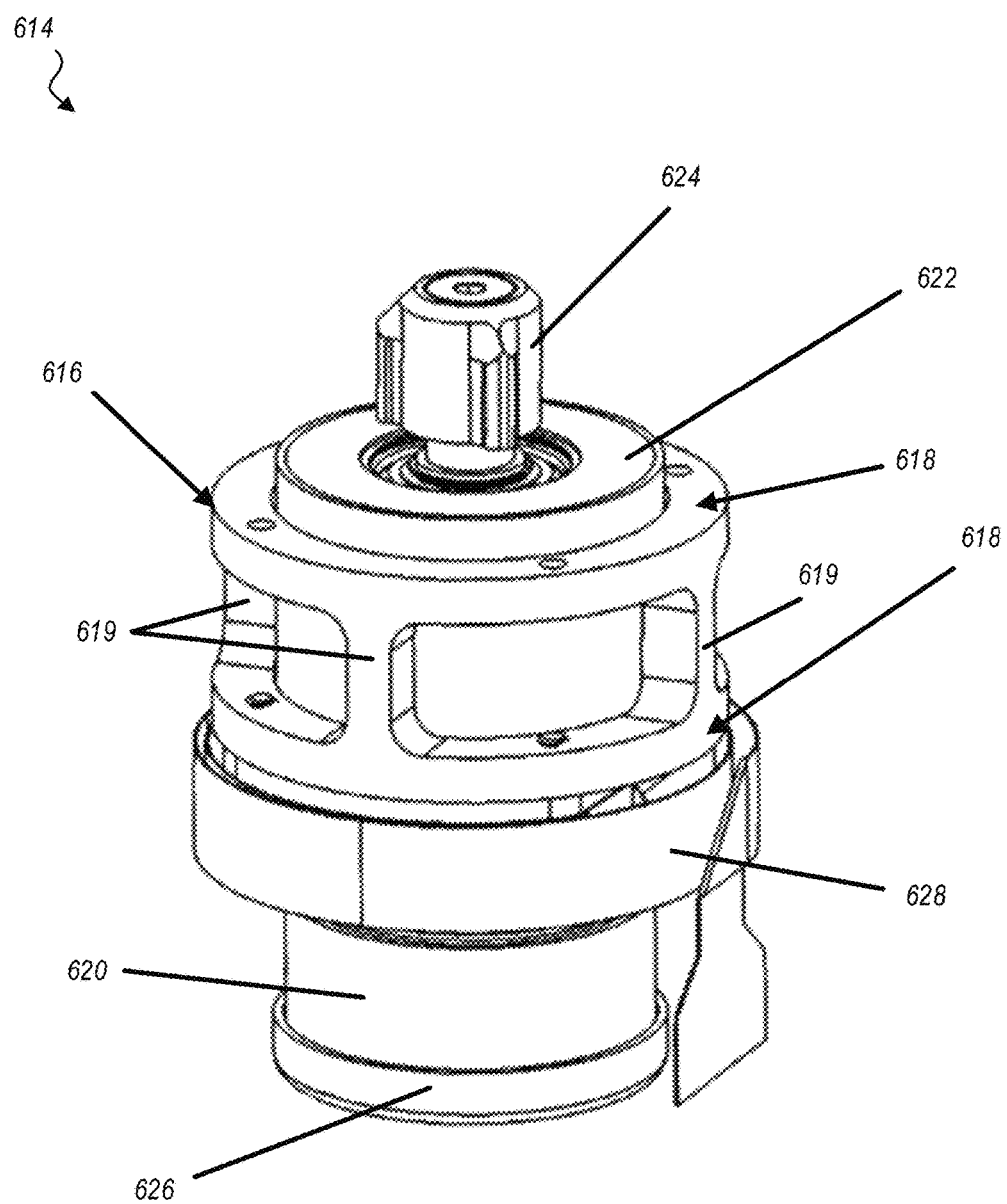
FIG. 7 is a perspective view of a compact height torque sensing articulation drive assembly system, according to an exemplary illustration.

Embodiments with less or more than four pullwires are contemplated by the present disclosure. When, for example, a four-wire catheter 304 is coupled to the instrument driver 108, each drive shaft 316 thereof is thereby coupled to a different respective wire 504-510 (see FIG. 6). As such, a distal articulation section 512 of the catheter 304 can be articulated and steered by selectively tightening and loosening pullwires 504-510. Typically, the amount of loosening and tightening is slight, relative to the overall length of the catheter 304. That is, each wire 504-510 typically need not be tightened or loosened more than perhaps a few centimeters. As such, the motor shafts that tighten/loosen each wire typically do not rotate more than, for example, ¾ of a rotation. Thus, given the solid mechanics and kinematics of directing the instrument driver, a catheter (or other flexible elongate instrument) may be controlled in an open-loop manner, in which the shape configuration command comes into the beam mechanics and is translated to beam moments and forces, then translated into pullwire tensions as an intermediate value before finally being translated into pullwire displacement given the entire deformed geometry. Based on the pullwire displacement command, a motor servo can apply the appropriate electrical current to produce the amount of rotation required to displace the pullwire.

Robotic systems use these algorithms to determine the displacement of the pullwires to achieve the desired articulation of a catheter. However, differences between predicted and actual catheter position can result from the reliance by the kinematic model on certain assumptions and the lack of certain information. With rigid kinematics, simple geometry can be used to predict the location of any point along the rigid object given the following information: (1) a reference coordinate system; (2) an origin, or point in any coordinate system attached to the object; and (3) an orientation in any coordinate system attached to the object. Even with rigid structures, external forces, even gravity, may disrupt the ability to solve the location equation given the information above. If the above information is not sufficient to accurately describe the position of one point of an object from another point on the same object, then additional information must be provided, like the weight of the object, the forces acting on the object, the strength of the object, etc.

Standard equations and constants, like Poisson's ratio, Hertzian stresses, Modulus of Elasticity, and linear stress/strain equations can improve on the kinematic model but these methods break down once the strains exceed the standard elastic range (usually about 3%). For example, a slim bar may be straight under no distal loading and the equations to predict the location of the distal end are fairly effective. However, when a load is placed on the beam, the distal end will deflect, or strain under the load. Even in a purely elastic response to the load, the location or orientation of the distal end of the beam is impossible to predict without knowing the magnitude, the direction, and the location of the external load. Similarly, flexible instruments such as catheters with low strength can be deflected by unknown loads at unknown locations and in unknown directions. Yet, prediction of the location and orientation of the distal end of a catheter is an important aspect of a robotic catheter system. The orientation of the distal end of the catheter based on information measured at the proximal end can better be determined through embodiments of the present disclosure.

The exemplary illustrations herein may be applicable to a variety of ideas for effectively measuring tension in catheter pullwires, tension in pullwires in other surgical instruments and/or tension in components of other surgical or endoscopic instruments. Tension sensing may be used to enable or improve pretensioning, catheter control, slack wire management, catheter failure detection, etc., (e.g., as discussed in U.S. Pat. No. 9,173,713, previously incorporated by reference). The specific concepts presented herein may be applicable to techniques for obtaining torque measurements on output shafts of an instrument driver. Each will be addressed in further detail below.

Figure 8:
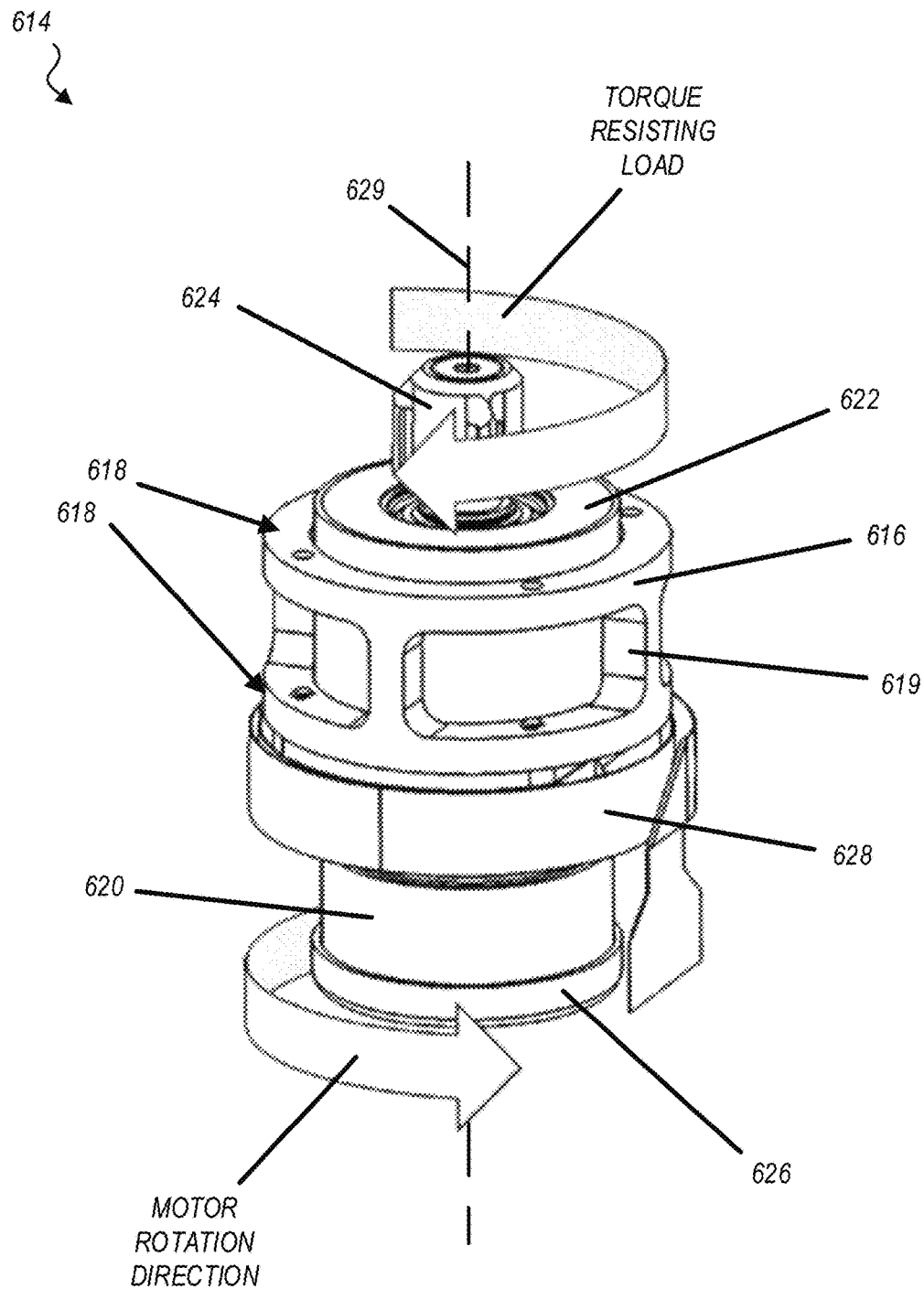
FIG. 8 is a perspective view of a compact height torque sensing articulation drive assembly system, including indications of motor rotation direction, torque resisting load, and an axis, according to an exemplary illustration.
Figure 9:
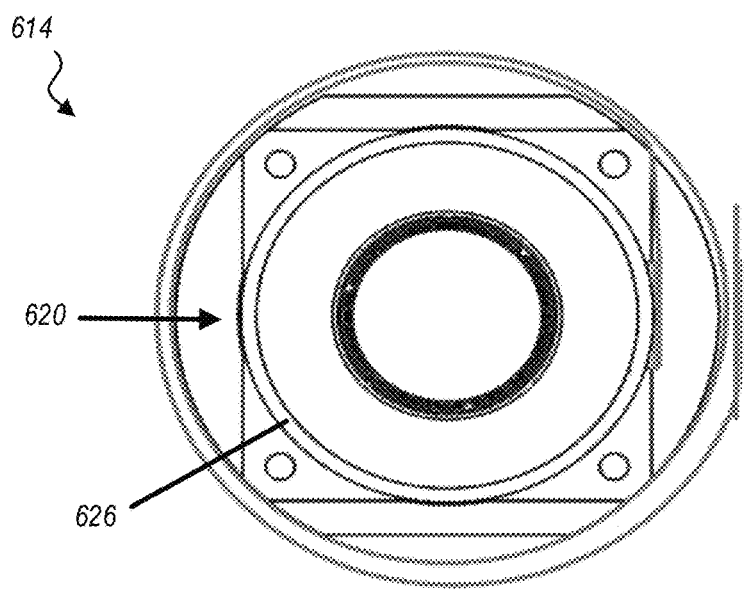
FIG. 9 is a bottom view of a compact height torque sensing articulation drive assembly system, according to an exemplary illustration.
Figure 10:
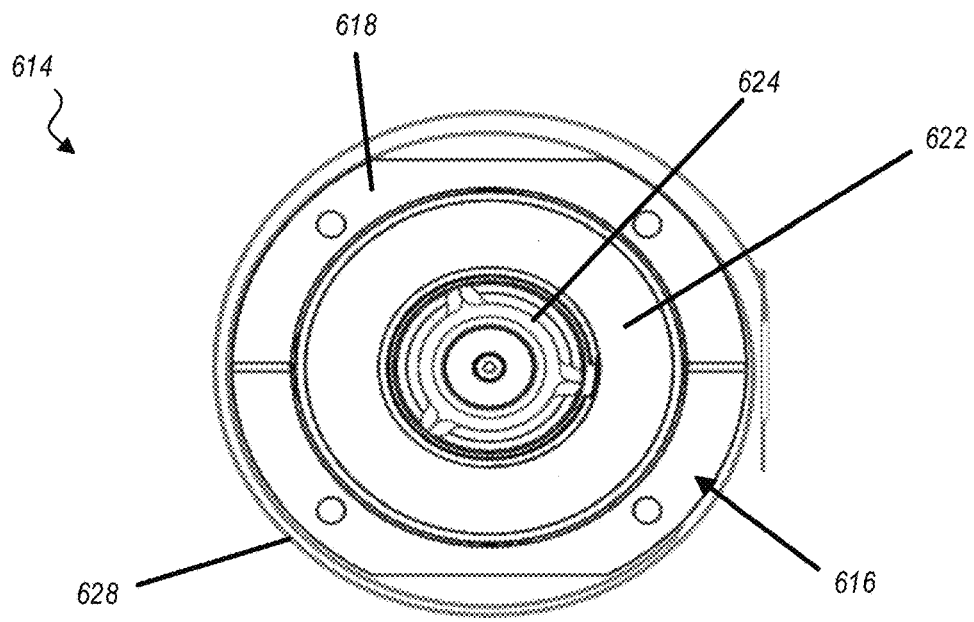
FIG. 10 is a top view of a compact height torque sensing articulation drive assembly system, according to an exemplary illustration.
Figure 11:
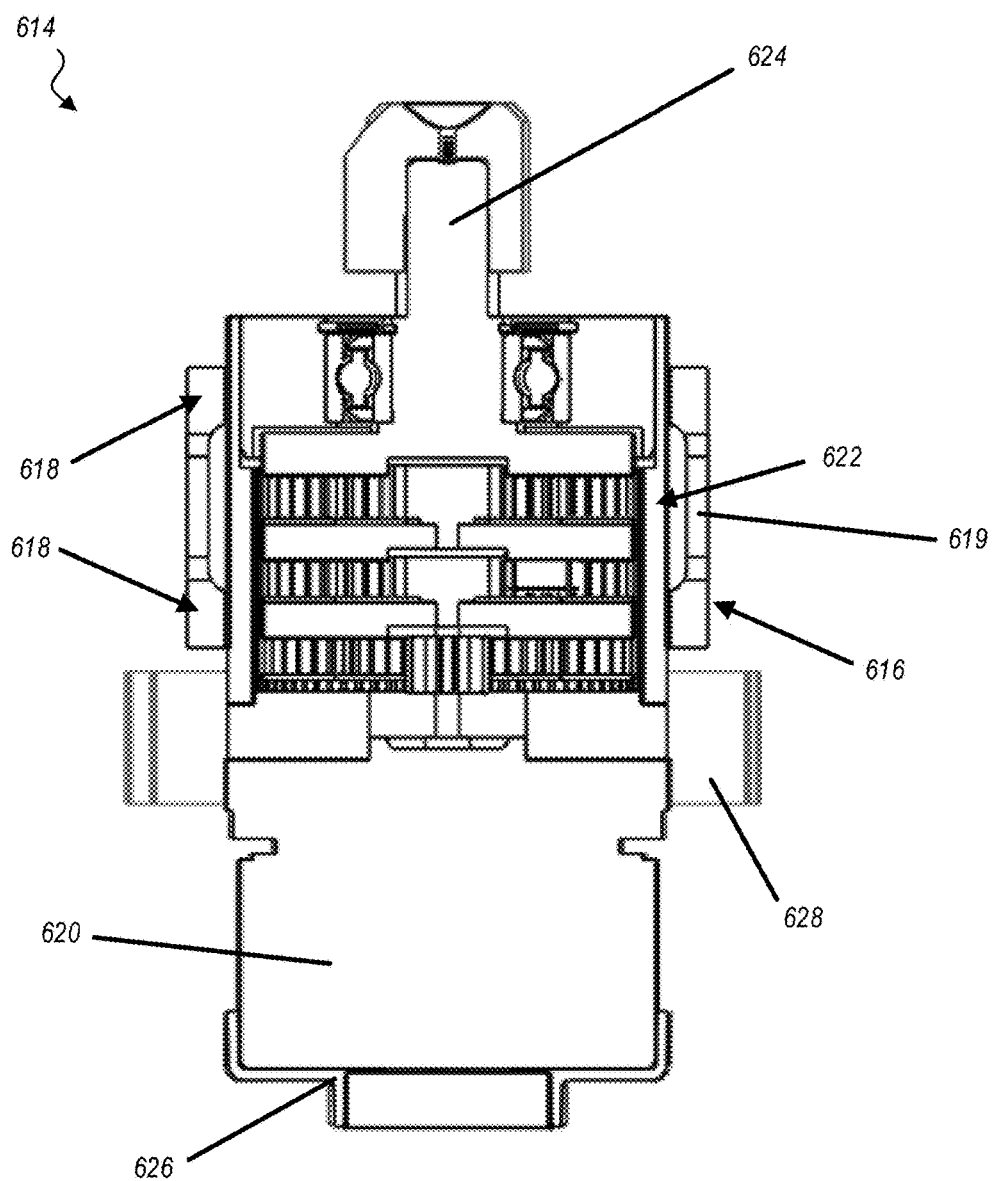
FIG. 11 is a cross section view of a compact height torque sensing articulation drive assembly system, according to an exemplary illustration.
Figure 12:
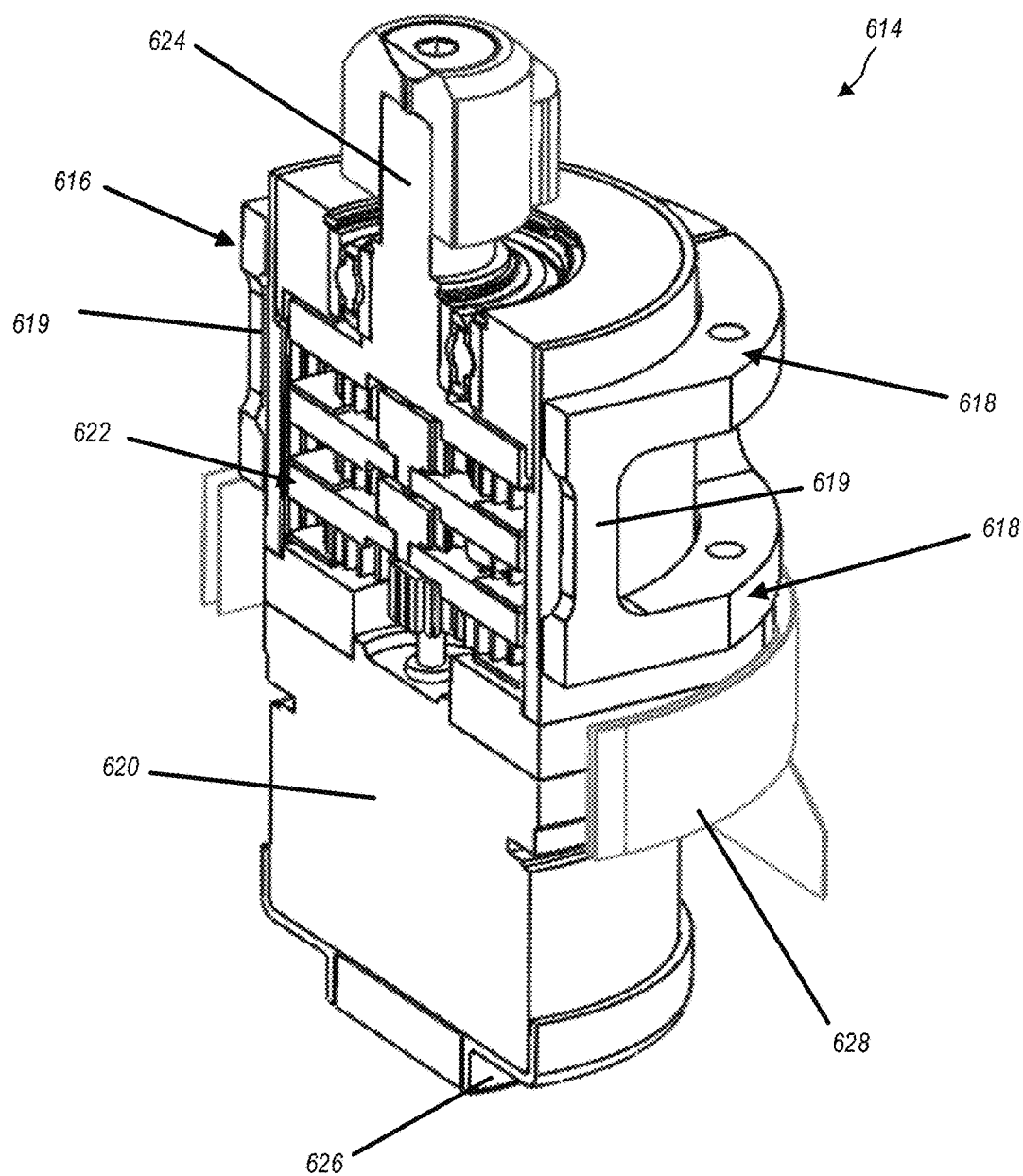
FIG. 12 is a cutaway view of a compact height torque sensing articulation drive assembly system, according to an exemplary illustration.
Figure 13:
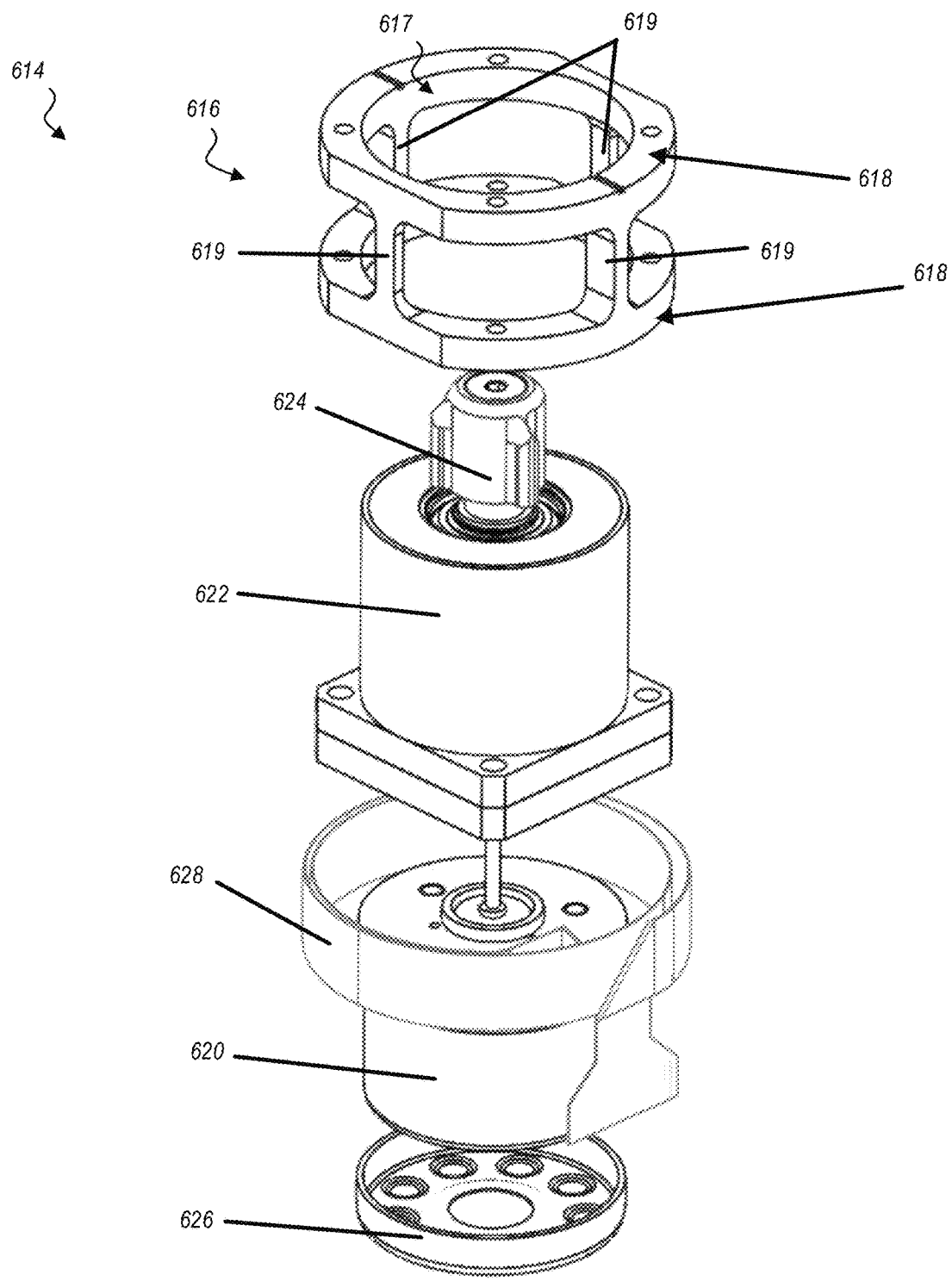
FIG. 13 is an exploded view of a compact height torque sensing articulation drive assembly system, according to an exemplary illustration.

FIGS. 7-13 illustrate embodiments of compact height torque sensing articulation drive assemblies 614, including a torque sensor 616 with mounting flanges 618, struts 619, a motor 620, a motor gearbox 622, a gearbox output shaft 624, an encoder 626, and a cable 628. The assembly 614 may be aligned along an axis 629 (see, e.g., FIG. 8). For example, the motor 620 and the gearbox 622 may be aligned end-to-end along the axis 629. The assembly 614 may sense tension on catheter pullwires in an articulating catheter or torque on a robotic output axis, which can correspond to the axis 629 shown in FIG. 8, using the torque sensor 616. In some embodiments, the assembly 614 may sense tension on catheter pullwires in an articulating catheter by sensing and/or determining the output torque (also referred to as output shaft torque) produced by the output shaft 624 along the robotic output axis 629 using the torque sensor 616. With reference to FIG. 8, the output shaft torque can be in a direction opposite to the torque resisting load applied to the output shaft 624. The output shaft 624, in some arrangements, can correspond to or be operatively coupled to drive shafts such as the drive shafts 314, 316 described above and/or other components.

The torque sensor 616 may be a component of the assembly configured to measure torque, and may act as a sensed mounting structure or load cell. It may be configured as a reactive torque sensor that measures torque induced strain using one or more self-contained strain gauges to create a load cell. The torque sensor 616 and components thereof may be configured to be communicatively coupled to another component or part of a system, such as the control system 113, in order to transmit and/or receive signals, such as a measured torque reading. For example, as explained further below, in some embodiments, the output torque produced by the motor 620 and/or gearbox 622 about the axis 619 can be measured or determined from a reaction torque required to prevent the motor 620 and/or gearbox 622 from turning. Advantageously, the use of a reactive torque sensor 616 may eliminate the need for a rotary signal transmission method, thereby reducing complexity and cost of the overall assembly 614. Advantageously, the use of the reactive torque sensor 616 according to certain embodiments described herein can result in a particularly compact torque sensor arrangement that can provide torque information to control a device used with an instrument driver without increasing the size or only minimally increasing the size of the instrument driver.

For clarity of description, as used herein, the terms "torque sensor," "reactive torque sensor," and "reaction torque sensor" interchangeably refer broadly, without limitation, to a device that converts a torsional mechanical input into an output such as an electrical signal and can be used to measure torque.

Figure 14A:
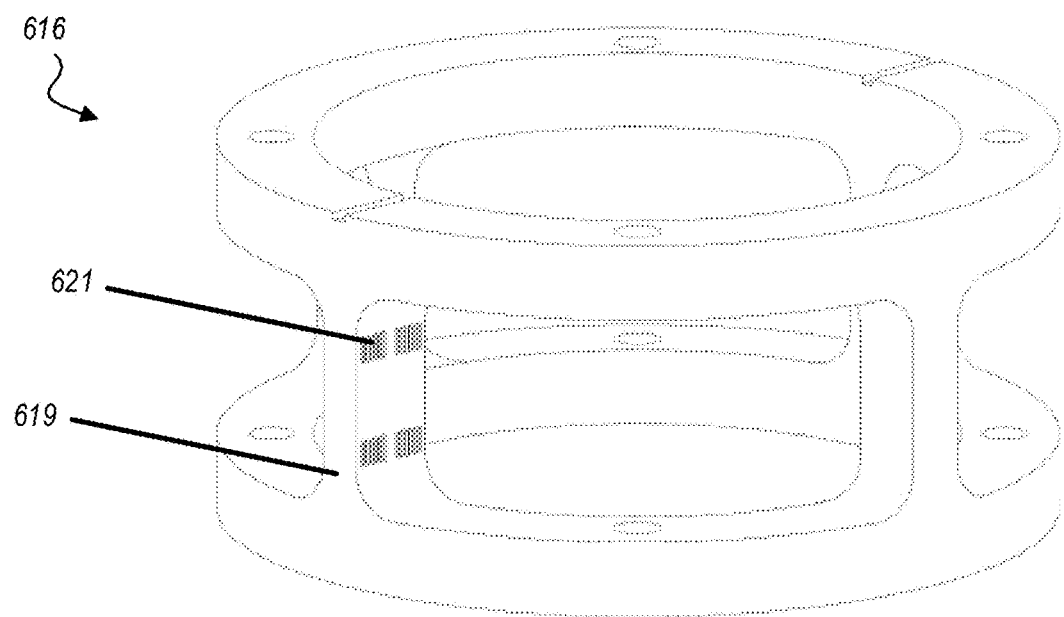
FIGS. 14A and 14B are perspective views of torque sensors showing the position of strain gauges, according to exemplary illustrations.
Figure 14B:
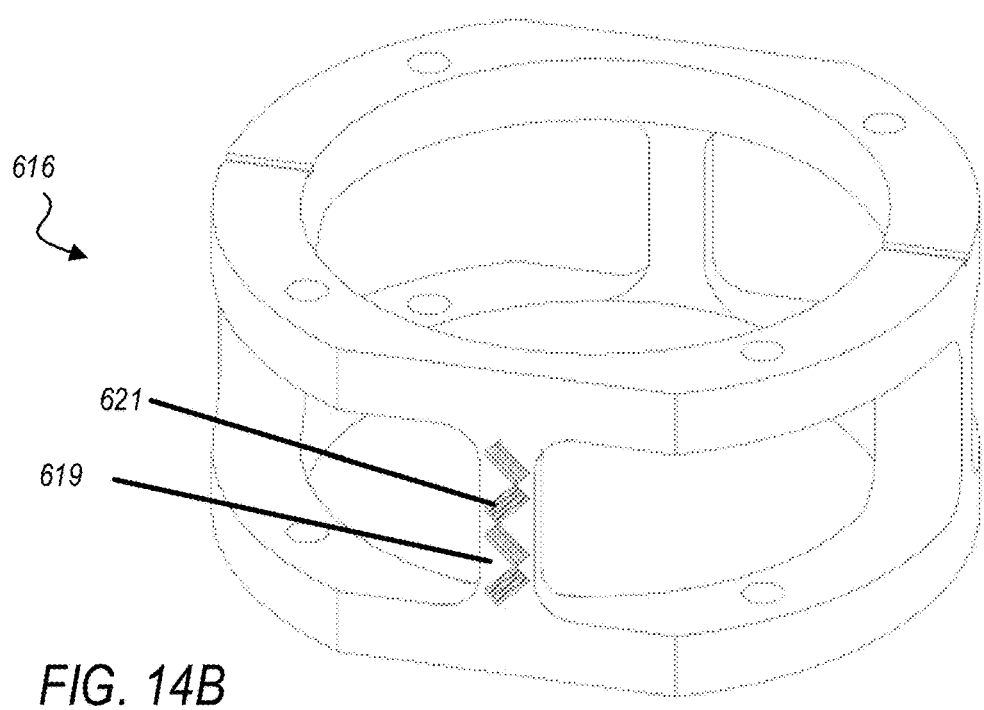

FIGS. 14A and 14B illustrate embodiments of torque sensors 616 showing example positions of strain gauges 621. The strain gauges 621 of the torque sensor 616 may be disposed in various locations on the struts 619 of the torque sensor 616. For example, strain gauges 621 may be placed on a side of the strut 619 to detect bending strain (see, e.g., FIG. 14A). In another example, the strain gauges 621 may be disposed on a circumferential face of struts 619 to detect shear strain (see, e.g., FIG. 14B). Strain gauges 621 may also be placed in several different locations on a strut to take several measurements. Depending on location, the strain gauges 621 may measure shear, compressive and/or tensile loads on the faces of the mounting structure and hence measure the induced torque on the structure.

FIG. 14A illustrates an embodiment of a torque sensor 616 having four strain gauges 621 mounted on a side wall of a strut 619. This configuration of the torque sensor 616 may be described as a bending strain gauge. FIG. 14B illustrates an embodiment of a torque sensor 616 having strain gauges 621 arranged in a zig-zag pattern on a circumferential face of a strut 619 of the torque sensor 616 such that loading of the torque sensor 616 causes stretching of the strain gauge 621 and an increased resistance across it. This arrangement may be described as a shear strain gauge sensor. In some embodiments, there may be strain gauges 621 mounted in a group of four to form a full Wheatstone bridge which ensures strain measurements are temperature compensated.

In some embodiments, the sensor 616 with integrated strain gauges 621 may be a flexure-based structure. In some embodiments, the torque sensor 616 may include mounting flanges 618 connected by struts 619 to create the flexure based structure. In some embodiments, the strain gauges 621 are attached to the struts 619 of the structure to ensure the strain is detected by a strain gauge 621. The length and thickness of the struts 619 of the flexure-based structure may be designed to allow a Wheatstone bridge or a strain gauge to sense torque-induced strain.

Figure 15A:
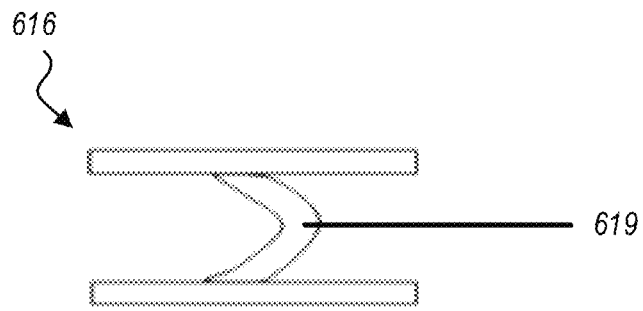
FIGS. 15A-15C are side views of configurations of struts of a torque sensor, according to exemplary illustrations.
Figure 15B:
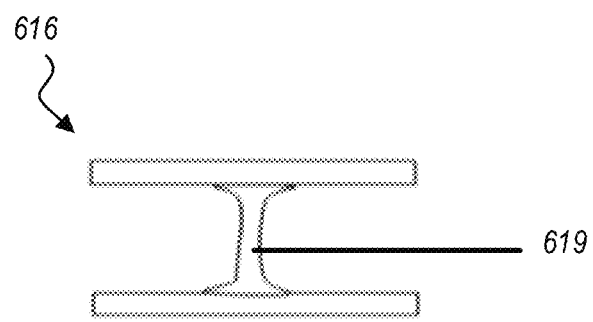
Figure 15C:
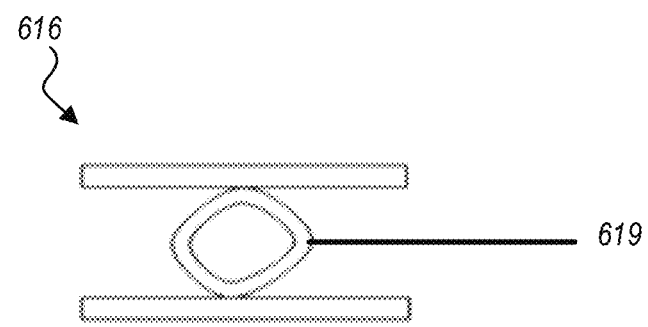

FIGS. 15A-15C illustrate several non-limiting examples of configurations for struts 619 of the torque sensor 616. FIG. 15A illustrates an embodiment of a torque sensor 616 having an arcuate strut 619. FIG. 15B illustrates an embodiment of a torque sensor 616 having a beam strut 619 shaped substantially like a dumbbell or serif "I". FIG. 15C illustrates an embodiment of a torque sensor 616 having a substantially annular strut 619. While FIGS. 15A-15C show various example strut shapes for a torque sensor, others are also possible. The strut shapes may be selected to optimize deformation and torque measurement.

The torque sensor 616 may be hollow, have an inner lumen, or be otherwise configured to be disposed around the motor 620, gearbox 622, and/or encoder 626. In one embodiment, the torque sensor may form a ring around the motor 620, gearbox 622, and/or encoder 626. The torque sensor 616 may partially or completely radially surround and be coaxial with a portion of or the entirety of the motor 620, the gearbox 622, and/or the gearbox output shaft 624. For example, the torque sensor 616 may define an opening 617 (see FIG. 13) that is sized and shaped to accommodate the motor 620, the gearbox 622, and/or the gearbox output shaft 624. The opening 617 may have a diameter or diagonal greater than a diameter or a diagonal of the motor 620 and/or the gearbox 622, such that the motor 620 and/or the gearbox 622 fit within the opening 617. The torque sensor 616 may be custom designed to fit in surrounding relation to the gearbox and/or motor. Advantageously, this configuration may have significantly lower height (e.g., at least 20% less height) than traditional arrangements. Accordingly, such a configuration facilitates the addition of torque sensing to articulation drive assemblies without adding any axial length to the assembly.

The assembly 614 may be configured such that the torque sensor 616 does not add any overall length to the assembly 614 along the axis 629. For example, the length of the assembly 614 along the axis 629 is the same length with or without the torque sensor 616. Some embodiments may be configured such that the torque sensor 616 does not add any overall length to the combined length of the motor 620 and the gearbox 622, such that the length of the motor 620 and the gearbox 622 combined is the same with or without the torque sensor 616. In some embodiments, the torque sensor 616 is shorter in length than the motor 620 and/or gearbox 622. In some embodiments, the torque sensor 616 is sized and shaped such that the motor 620, gearbox 622, and/or gearbox output shaft 624 do not extend radially beyond the torque sensor 616. The torque sensor 616 may circumscribe the motor 620 and/or the gearbox 622.

The torque sensor 616 may be configured to provide a main grounded mounting structure for the motor 620, the gearbox 622, and/or the encoder 626, which may otherwise be suspended and free floating. For example, one or more of the motor 620, the gearbox 622, and the encoder 626 may be mounted to the torque sensor 616 using one or more mounting flanges 618 or other component. The mounting flanges 618 may have any suitable shape and structure that facilitates mounting or attachment of the torque sensor 616 to another component. The mounting flanges 618 may include an upper flange and a lower flange. In some embodiments, the mounting flanges may form a ring. The upper flange may be a flange that is closer to the output shaft 624 than a lower flange. In some embodiments, a flange (e.g., the lower flange) may be mounted to the motor 620 and/or the gearbox 622. In some embodiments, a flange (e.g., the upper flange) or another part of the torque sensor 616 may ground torque loads by attaching to an instrument driver housing or another grounded structure. For example, a flange may be grounded to the chassis of an instrument. Thus, in some embodiments, the torque produced by the motor 620 and/or gear box 622 about the axis 619 (see FIG. 8) can be measured to determine the reaction torque required to prevent the motor 620 and/or gearbox from turning 620. Thus, torque loads can be grounded by coupling a flange (e.g., the upper flange) to a grounded structure while the other flange (e.g., the lower flange) can be coupled to the motor 620 and/or gearbox 620. Torque induced strain along the torque sensor 616 can be measured by the strain gauges 621 to measure or determine the reaction torque which can be used to measure or determine output torque of the motor 620. The output torque can be used, for example, to determine tension in catheter pullwires in an articulating catheter and/or in other components of a robotic surgical system (e.g., the robotic surgical system 100). In some embodiments, the measured or determined output torque can be used by the control system 113 or other component to measure or determine tension in catheter pullwires, tension in pullwires of other surgical instruments and/or tension in of components of other surgical or endoscopic instruments. The control system 113 or other components can also use this information to enable or improve pretensioning, catheter control, slack wire management, catheter failure detection, etc.

Figure 16A:
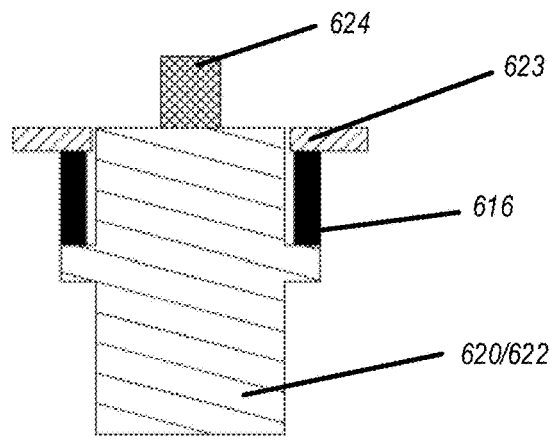
FIGS. 16A-16C are cutaway views of arrangements between a torque sensor, a motor, a gearbox, a grounded structure, and an output shaft, according to exemplary illustrations.
Figure 16B:
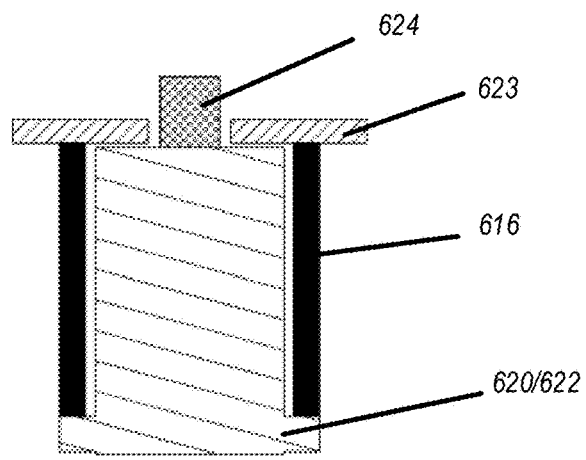
Figure 16C:
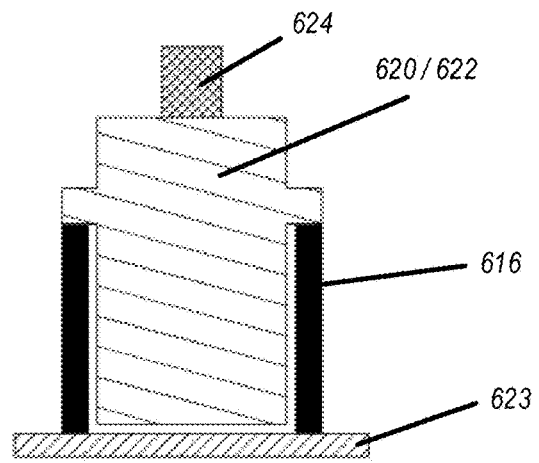

FIGS. 16A-16C illustrate several non-limiting embodiments of arrangements between a torque sensor 616, a motor 620, a gearbox 622, a grounded structure 623, and an output shaft 624. In particular, FIG. 16A illustrates an embodiment having a motor/gearbox 620/622 mounted below a grounded structure 623 via a torque sensor 616 mounted approximately at a mid-point of the motor/gearbox 620/622 with the output shaft extending beyond the grounded structure 623. The top of the motor/gearbox 620/622 is approximately flush with a top portion of the grounded structure 623. FIG.

16B illustrates an embodiment having a motor/gearbox 620/622 mounted below a grounded structure 623 via a torque sensor 616 mounted approximately at a base of the motor/gearbox 620/622. The top of the motor/gearbox 620/622 is below the grounded structure 623 with the output shaft 624 extending beyond the grounded structure 623. FIG. 16C illustrates an embodiment having a motor/gearbox 620/622 mounted above a grounded structure 623 via a torque sensor 616 mounted at an upper portion of the motor/gearbox 620/622. While FIGS. 16A-16C show various example arrangements, others are also possible.

In some embodiments, the motor 620 may be a brushless low-profile outrunner motor 620; however, other kinds of motors may be used. In some embodiments, the gearbox 622 may be configured to increase torque and decrease rotational speed that is output from the motor 620, but other configurations may also be used. The output shaft 624 may be directly or indirectly connected to a component of a system to be driven (e.g., an elongate member). The encoder 626 may be any kind of measurement device configured to measure the rotational movement of one or more components. The encoder 626 may be an optical encoder, a magnetic encoder, or other kind of encoder. The cable 628 may be a cable for transmitting energy or signals and may be communicatively coupled to one or more of the torque sensor 616, the motor 620, the gearbox 622, the encoder 626 and/or other components. The cable 628 may be configured as a clock spring wound flat flex cable, which may minimize the torsional resistance that motor leads would normally produce. The cable may also be configured as a different kind of wrapped or other cabling system. The wound or wrapped configuration of the cable 628 may increase the usable resolution of the torque sensor 616. The cable 628 may be axially aligned with and surround or partially surround the torque sensor 616, motor 620, and gearbox 622.

While the various components of the assembly 614 have been illustrated as separate components, they need not be. For example, the gear box 622 may be incorporated into the motor 620. As another example, the torque sensor 616 need not be a separate apparatus. It may be integrated into a wall of the gearbox or motor, into a housing or grounded plane 623, and/or into another structure.

Figure 17A:
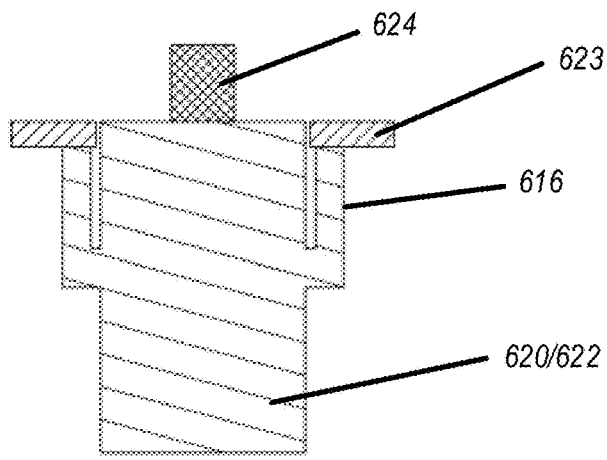
FIGS. 17A-17C are cutaway views of configurations of a torque sensor, a motor/gearbox, a grounded structure, and an output shaft, according to exemplary illustrations.
Figure 17B:
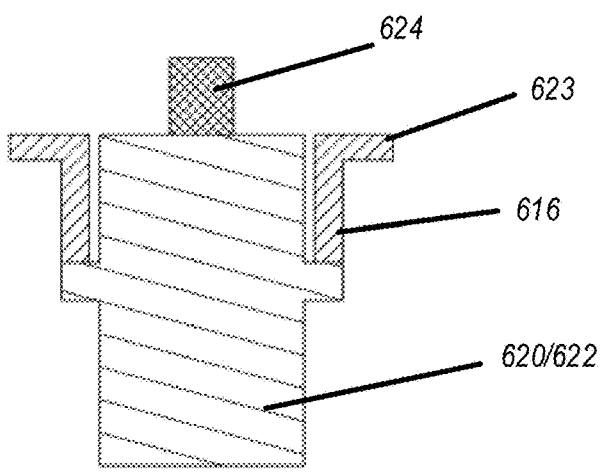
Figure 17C:
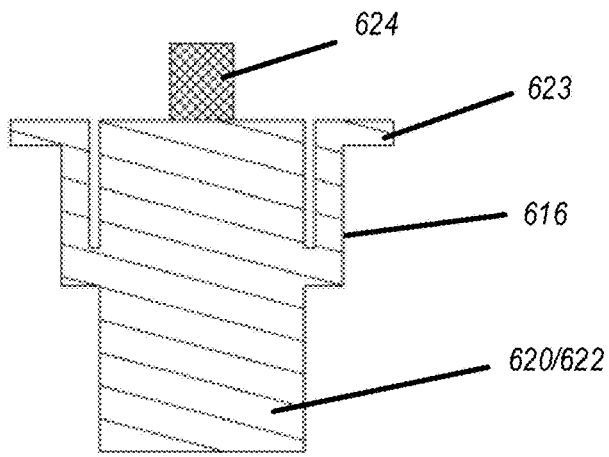

FIGS. 17A-17C illustrate several non-limiting configurations of a torque sensor 616, a motor/gearbox 620/622, a grounded structure 623, and an output shaft 624. In particular, FIG. 17A illustrates an embodiment wherein the torque sensor 616 is integrated into a wall of the gearbox/motor 620/622 and mounted to the grounded structure 623. FIG. 17B illustrates an embodiment where the torque sensor 616 is integrated into the grounded structure 623 and mounted to the motor/gearbox 620/622. FIG. 17C illustrates an embodiment where the torque sensor 616, the motor/gearbox 620/622, and the grounded structure 623 are integrated with one another.

Figure 18:
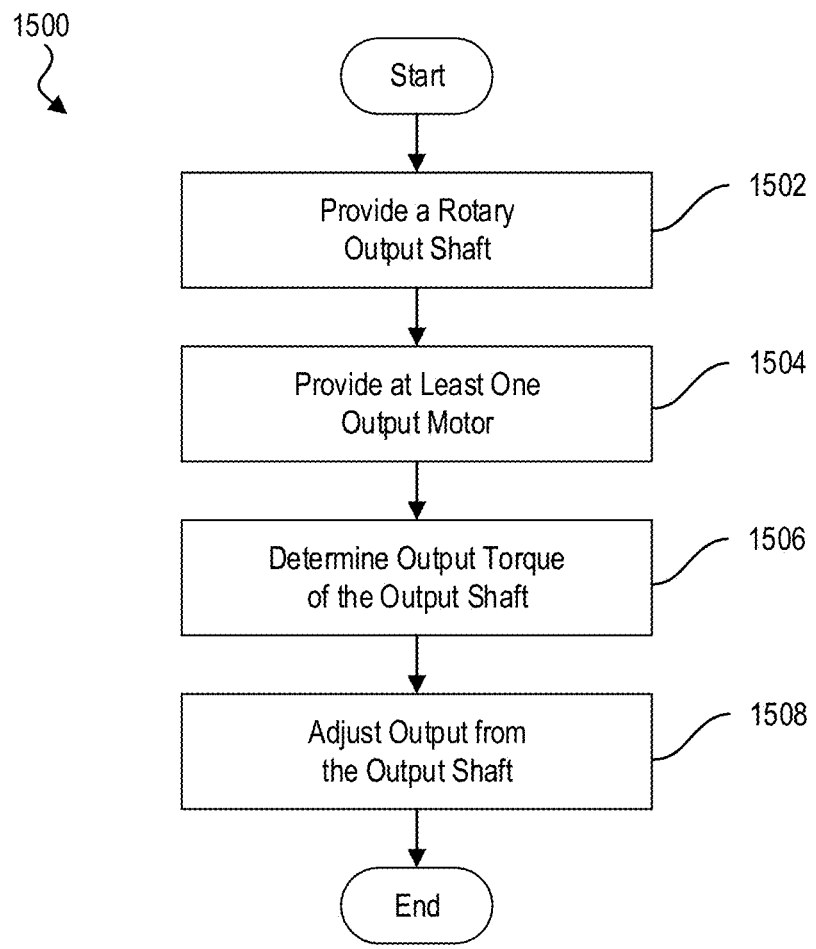
FIG. 18 is a process flow diagram for an exemplary method of measuring an output torque.

FIG. 18 illustrates an example process 1500 for controlling an output torque. At block 1502 of the process 1500, a rotary output shaft is provided. For example, exemplary rotary output shafts are described above for actuating an elongate member (e.g., by actuating one or more pull wires of the elongate member).

At block 1504, at least one output motor is provided. For example, as described above, exemplary output motors may be configured to actuate movement of the elongate member by rotating the output shaft.

At block 1506, an output torque of the output shaft is detected or determined (e.g., based at least upon one sensor input). In an example, a load beam, load cell, or a torque sensor (e.g., as described above as torque sensor 616) may be employed. In examples where a load cell is employed, the load cell may be configured to measure the output shaft torque based upon at least a deflection of the load cell. In an example, load cells may have a cantilever mounting within the instrument driver. In various embodiments, the output torque is detected or determined utilizing a torque sensor assembly disposed around one or more of the provided output shaft and output motor, as described above.

At block 1508, rotation of the output shaft may be modified (e.g., by adjusting one or more parameters of a motor or gearbox) based on the output torque. By modifying the rotation of the output shaft, tension on a pull wire coupled to the output shaft may be modified. Such a pull wire may be disposed within an elongate member. This may, for example, impart a bend or other motion to an articulating section of the elongate member. In another example, modifying the output from the output shaft may actuate a roller of an active drive system.

In one example embodiment of use for controlling output torque and/or controlling movement of an elongated member can include actuating movement of an elongated member by rotating an output shaft with a motor. Some embodiments can include detecting or determining output torque of the output shaft based at least in part upon a sensor input. For example, the sensor input can be based upon the torque induced strain along a torque sensor which can be disposed around one or more of the output shaft or motor (e.g., as the reactive torque sensor 616 described herein). The method can also include actuating the motor in response to the measured or determined output torque to drive the output shaft. The rotation of the output shaft 624 can be modified (e.g. by adjusting one or more parameters of a motor or gearbox) based on the measured or determined output torque. The method of use can include modifying tension on a pull wire or another element of the system by modifying rotation of the output shaft in response to the measured or determined output torque. In some embodiments, the control system 113 is configured modify rotation of the output shaft in response to the measured or determined output torque.

In various embodiments, by determining and selectively modifying the output torque (e.g., rotation of the output shaft), the output torque can be carefully controlled. In some embodiments, this control enables a robotic catheter system to precisely and accurately tension one or more pull wires in an elongate member so that the resultant articulation of the elongate member precisely and accurately reflects the articulation commanded by a user at an input device based on improved modeling of predicted catheter tip movement.

The exemplary systems and components described herein (e.g., workstation 112, electronics rack 118, the control system 113, the exemplary instrument drivers, and/or any components thereof) may include a computer or a computer readable storage medium or computer readable memory that has stored thereon executable instructions and there can be one or more processors in communication with the computer readable memory that are configured of execute the instructions to implement the operation of drive and implement the various methods and processes described herein. In general, computing systems and/or devices, such as user input devices included in the workstation 112 and/or the control system 113 or any components thereof, merely as examples, may employ any of a number of computer operating systems, including, but by no means limited to, versions and/or varieties of the Microsoft Windows operating system, the Unix operating system (e.g., the Solaris operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium or computer readable memory) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that include a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may have such instructions stored on computer readable media for carrying out the functions described herein.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many examples and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A robotic surgical system, comprising:
   a control system configured to be connected to an input device and to receive information for positioning or orienting a catheter from the input device; and
   an instrument driver operatively connected to the control system, the instrument driver including:
      a motor configured to provide rotary output to actuate movement of an elongate member;
      a gearbox configured to modify the rotary output of the motor; and
      a reactive torque sensor coaxial with and radially surrounding at least one of the motor and the gearbox,
   wherein the control system is configured to actuate the motor in response to the information to drive an output shaft in communication with the elongate member; and wherein the reactive torque sensor is configured to determine an output shaft torque imparted by the output shaft.

2. The robotic surgical system of claim 1, wherein the torque sensor does not substantially add to an overall length to the instrument driver along the longitudinal axis.

3. The robotic surgical system of claim 1, wherein the reactive torque sensor provides a grounded mounting structure for the motor and the gearbox.

4. The robotic surgical system of claim 1, wherein at least one of the gearbox and the rotary motor is mounted to the reactive torque sensor by a first mounting flange and wherein torque sensor is mounted to the instrument driver by a second mounting flange.

5. The robotic surgical system of claim 4, wherein at least one of the first and second mounting flanges is integrally formed with a wall of the motor or gearbox.

6. The robotic surgical system of claim 4, wherein at least one strain gauge is placed on one or more struts placed between the first mounting flange and the second mounting flange.

7. The robotic surgical system of claim 6, wherein the at least one strain gauge is configured to measure bending strain or shear strain.

8. The robotic surgical system of claim 7, wherein the first mounting flange forms a first ring and the second mounting flange forms a second ring that is coaxial with the first ring.

9. The robotic surgical system of claim 8, wherein the one or more strut extends from the first ring to the second ring.

10. The robotic surgical system of claim 1, wherein the instrument driver is configured to adjust a pullwire tension to impart motion to a tip of the catheter.

11. The robotic surgical system of claim 1, wherein the reactive torque sensor further comprises at least one strain gauge configured to measure the output shaft torque.

12. The robotic surgical system of claim 11, wherein the at least one strain gauge is placed on one or more struts placed between a first mounting flange and a second mounting flange.

13. The robotic surgical system of claim 12, wherein the at least one strain gauge is configured to measure bending strain or shear strain.

14. The robotic surgical system of claim 1, comprising a grounded structure for supporting the motor and gearbox and wherein the reactive torque system comprises a mounting flange that couples at least one of the motor or gear box to the grounded structure.

15. An instrument driver for an elongate member of a robotic surgical system, comprising one or more drive assemblies, each assembly comprising:
a gearbox configured to actuate movement of the elongate member by driving an output shaft in communication with the elongate member;
a rotary output motor configured to drive the gearbox; and
a reactive torque sensor radially surrounding the gearbox and configured to determine an output shaft torque imparted by the output shaft to the elongate member.

16. The instrument driver of claim 15, wherein the torque sensor adds no axial length to the drive assembly.

17. The instrument driver of claim 15, wherein the reactive torque sensor provides a grounded mounting structure for the motor and the gearbox.

18. The instrument driver of claim 15, wherein the rotary output motor is a brushless motor.

19. The instrument driver of claim 15, wherein at least one of the gearbox and the rotary motor is mounted to the reactive torque sensor by a first mounting flange and wherein torque sensor is mounted to the instrument driver by a second mounting flange.

20. The instrument driver of claim 19, wherein the reactive torque sensor further comprises at least one strain gauge configured to measure the output shaft torque.

21. The instrument driver of claim 20, wherein the at least one strain gauge is placed on one or more struts placed between the first mounting flange and the second mounting flange.

22. A method of controlling a robotic surgical system, comprising:
rotating a rotary output shaft with a motor that drives the output shaft; and
determining an output torque of the output shaft using a torque sensor disposed in surrounding relation to the motor.

23. The method of claim 22, comprising using the determined output torque to determine tension in an elongated member operatively coupled to the output shaft.

24. The method of claim 23, wherein the elongated member is a pullwire.

25. The method of claim 23, further comprising using the determined tension to perform at failure detection in the robotic surgical system.

26. A compact height apparatus for measuring an output torque, comprising:
a housing comprising a motor configured to provide rotary output via an output shaft; and
a reactive torque sensor circumferentially surrounding the motor, the reactive torque sensor having a first flange attached to the housing and a second flange attached to the motor,
wherein the reactive torque sensor measures torque relative to the housing.

27. The compact height apparatus of claim 26, wherein the reactive torque sensor adds no axial length to the motor.

28. The compact height apparatus of claim 26, wherein the reactive torque sensor provides a grounded mounting structure for the motor.

29. The compact height apparatus of claim 26, wherein the motor is a brushless motor.

30. The compact height apparatus of claim 26, further comprising an encoder attached to the motor.

31. The compact height apparatus of claim 26, further comprising a gearbox attached to the motor.

32. The compact height apparatus of claim 31, wherein at least one of the gearbox and the motor is mounted to the reactive torque sensor by the first flange and wherein the torque sensor is mounted to the instrument driver by the second flange.

33. The compact height apparatus of claim 26, wherein the reactive torque sensor further comprises at least one strain gauge configured to measure an output shaft torque.

34. The compact height apparatus of claim 33, wherein the at least one strain gauge is placed on one or more struts placed between the first flange and the second flange.

* * * * *